United States Patent [19]

Zuest et al.

[11] Patent Number: 5,417,570
[45] Date of Patent: May 23, 1995

[54] DENTAL ANCHOR ASSEMBLY

[75] Inventors: Max Zuest, San Diego; Paul Zuest, Poway, both of Calif.

[73] Assignee: Zest Anchors, Inc., Escondido, Calif.

[21] Appl. No.: 176,597

[22] Filed: Jan. 3, 1994

[51] Int. Cl.[6] .................................. A61C 13/12
[52] U.S. Cl. .............................. 433/177; 433/173; 433/172
[58] Field of Search ............ 433/173, 174, 175, 176, 433/181, 177

[56] References Cited

U.S. PATENT DOCUMENTS

| | | | |
|---|---|---|---|
| 711,324 | 10/1902 | Lacy. | |
| 866,304 | 9/1907 | Roach | 433/177 |
| 3,514,858 | 6/1970 | Silverman. | |
| 3,787,975 | 1/1974 | Zuest | 433/183 |
| 4,290,755 | 9/1981 | Scott | 433/173 |
| 4,431,416 | 2/1984 | Niznick | 433/174 |
| 4,488,874 | 12/1984 | Soyer | 433/173 |
| 4,488,875 | 12/1984 | Niznick | 433/173 |
| 4,540,367 | 9/1985 | Sulc | 433/181 |
| 4,645,453 | 2/1987 | Niznick | 433/173 |
| 4,738,623 | 4/1988 | Driskell | 433/173 |
| 4,780,080 | 10/1988 | Haris | 433/173 |
| 4,793,808 | 12/1988 | Kirsch | 433/173 |
| 4,832,601 | 5/1989 | Linden | 433/173 |
| 4,907,969 | 3/1990 | Ward | 433/173 |
| 4,934,935 | 6/1990 | Edwards | 433/174 |
| 4,957,438 | 9/1990 | Bax | 433/180 |
| 4,988,297 | 1/1991 | Lazzara et al. | 433/173 |
| 5,120,222 | 6/1992 | Sulc | 433/181 |
| 5,194,000 | 3/1993 | Dury | 433/173 |

FOREIGN PATENT DOCUMENTS

| | | | |
|---|---|---|---|
| 3406448 | 8/1984 | Germany | 433/174 |
| 9210145 | 6/1992 | WIPO | 433/173 |

*Primary Examiner*—Cary E. O'Connor
*Attorney, Agent, or Firm*—Brown, Martin, Haller & McClain

[57] ABSTRACT

A multiple part anchor assembly is designed for attaching a dental appliance to a non-vital tooth root or an implant, and has a female part for attachment to a tooth root or implant, a male part or stud having a first end for releasable snap engagement in a socket in the female part with some relative movement permitted between the parts, a cap for securing in a recess in a dental appliance having a second socket, and the male part having a swivel joint at its opposite end for engagement in the second socket to secure the root or implant to the appliance, the hinge joint allowing hinging of the stud relative to the cap.

38 Claims, 2 Drawing Sheets

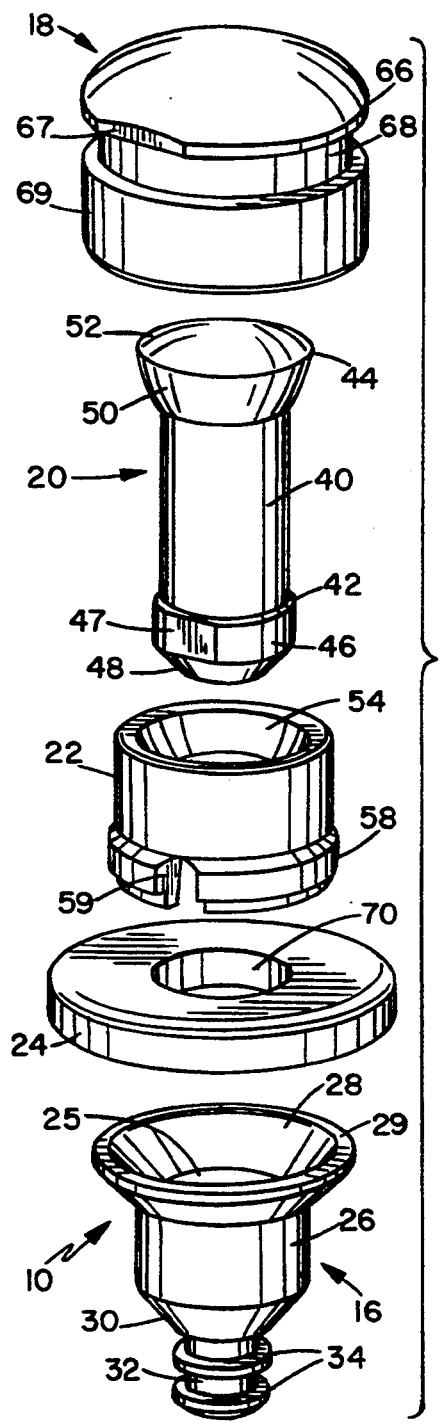
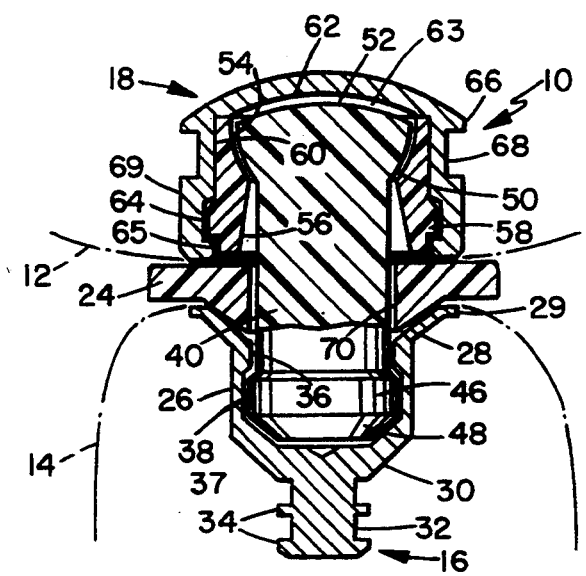
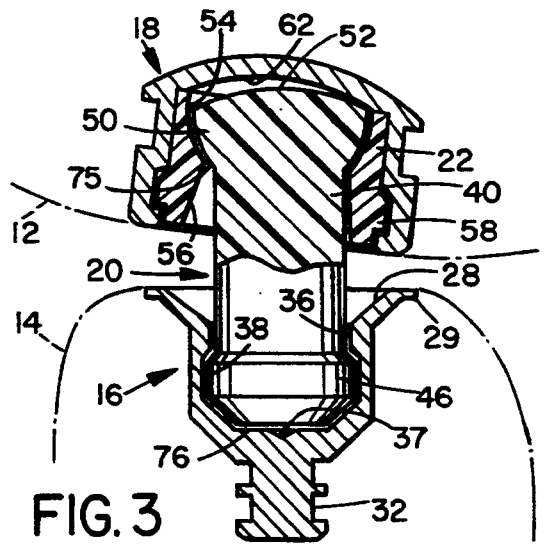
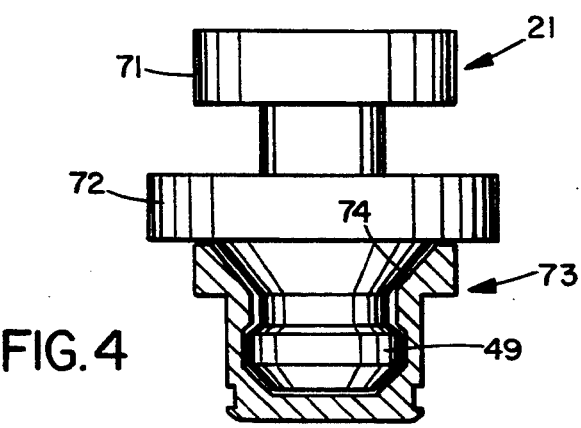
FIG. 1
FIG. 2
FIG. 3
FIG. 4

5,417,570

DENTAL ANCHOR ASSEMBLY

BACKGROUND OF THE INVENTION

The present invention relates to dental attachment systems or anchors for attaching dental appliances such as overdentures, partial dentures and the like to a remaining non-vital root or to an endosseus implant.

In U.S. Pat. No. 3,787,975 of Max Zuest, an anchor is described which comprises a socket element for insertion in a tooth root and a pivot pin which is embedded at one end in a denture and has an opposite end designed for pivotal snap engagement in the socket element. The pivoting end of the pin is of spherical shape and the socket element has a socket of matching shape.

One problem with existing anchors of this type is that the engaging surfaces of the pin and socket may become worn with repeated removal and insertion of the denture, so that the anchor becomes too loose to provide sufficient retention force for the appliance. Also, breakage or damage to the pin may occur over time, and it is difficult to replace a damaged pin since it is permanently secured to the appliance.

SUMMARY OF THE INVENTION

It is an object of the present invention to provide a new and improved anchor assembly for a dental appliance.

According to the present invention, an anchor assembly is provided which comprises a female socket member for attachment to a tooth root or implant, the socket member having a first socket, a male stud having a head at a first end shaped for releasable snap engagement in the socket and a swivel joint at the opposite end, a cap for connection to a dental appliance, the cap having a second socket, the swivel joint being adapted for engagement in the second socket in the cap, and allowing hinge motion of the stud relative to the cap.

Preferably, some rotational movement is also permitted between the first end of the stud and the first socket, so that movement is provided at both ends of the attachment, both where it attaches to the tooth root or implant, and where it attaches to the cap. However, since the major hinging action occurs at the cap rather than the root or implant, wear of parts resulting in loosening at the releasable attachment point is reduced.

The cap is permanently secured to the denture or other appliance, and is preferably of metal, while the stud or male member is of resilient material such as plastic and can be removed from the cap and replaced if necessary as a result of wear or breakage. Preferably, the stud has enlarged heads at both ends, the first head at the first end of the stud having a cylindrical outer periphery or band of larger diameter than the stud for engagement in a corresponding ring-shaped portion of the first socket. This provides a cylindrical retention band between the parts, and reduces wear due to the increased area of engagement between the parts.

The second head at the second end of the stud preferably has an at least partially spherical surface, and a retainer ring is releasably engagable with the second end of the stud for securing the second end in the second socket, the retainer ring encircling the second head and having a corresponding partially spherical seat for hinging engagement with the partial spherical surface on the second head, forming the hinge joint. Preferably, the retainer ring and second socket have corresponding snap-lock formations for snap lock engagement of the ring and second head of the stud in the second socket.

This arrangement allows the male or stud to be removed and replaced with a new male and snap lock retainer ring in the same permanent cap, without removing any denture acrylic. The double hinging action at both ends of the stud helps to keep the denture or appliance closer to the tissue, since the denture will tend to move more in a horizontal plane. This reduces the amount of food build-up under the denture. Because most of the movement occurs at the denture side of the anchor, there will be less wear at the tooth or implant side, and less risk of loosening of the anchor with time.

According to another aspect of the invention, an anchor assembly is provided for securing a dental appliance to a divergent implant extending at an angle to the desired path of insertion of the appliance. The assembly includes a base part having a stem for securing in a matching bore of a divergent implant, and a tapered socket, and an angled abutment having a tapered portion of taper matching that of the socket, for securing into the socket. The abutment has an angled socket extending at an angle to the central axis of the tapered portion, whereby the abutment can be rotated relative to the tapered socket to adjust the orientation of the angled socket until it substantially matches the desired direction of insertion of the appliance. At this point, the tapered portion is force-locked into the tapered socket. A male stud secured at one end to a dental appliance has a head at the opposite end for snap lock engagement in the appropriately oriented angled socket.

Angled abutment will be provided with sockets at different angles. This allows anchoring to divergent implants extending at various angles and in any direction.

BRIEF DESCRIPTION OF THE DRAWINGS

The present invention will be better understood from the following detailed description of some preferred embodiments of the invention, taken in conjunction with the accompanying drawings, in which like reference numerals refer to like parts, and in which:

FIG. 1 is a perspective view of the separated components of an anchor according to a first embodiment of the invention;

FIG. 2 is a side elevational view, partially sectioned, of the assembled components;

FIG. 3 is a similar view with the centering sleeve removed and showing the pivoting action;

FIG. 4 is a side elevation view, partially cut away, of impression male and female model parts for use in forming a master cast during laboratory assembly of a dental appliance using the anchor assembly of FIG. 1;

DESCRIPTION OF THE PREFERRED EMBODIMENTS

Figure 6:
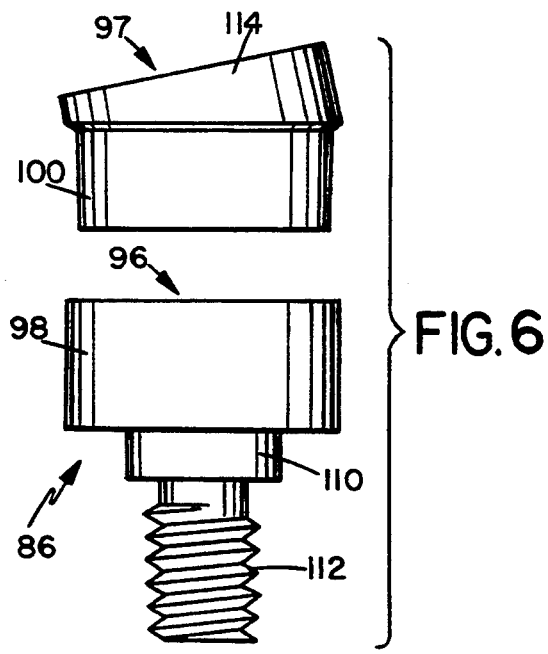
FIG. 6 is a side elevation view of the separated components of an alternative female element with an angled socket.

FIG. 1 illustrates the components of an anchor assembly 10 according to a first embodiment of the invention for attaching a dental appliance 12 such as an over-denture or partial denture to a remaining non-vital root 14, as illustrated in FIG. 2. The anchor assembly 10 basically comprises a female or socket part 16 for securing in a correspondingly shaped cut-out or recess in root 14, a cap 18 for securing in a correspondingly shaped cut out in appliance 12, and a stud or male part 20 for attaching the socket part 16 to the cap 18. Preferably, the cap and female part are both of metal while the pin or stud 20 is of resilient plastic material. Also included in the assembly are a retainer ring 22 for securing the stud 20 to the cap 18, and a centering sleeve 24 for preventing movement of the male part during processing.

The female or socket part 16 is of relatively strong material such as surgical steel coated with hardened titanium nitride for better bonding or osseointegration with the tooth. The female part 16 has an upwardly facing bore or socket 25, and a generally cylindrical body 26 with an outwardly tapered rim 28 and annular flange 29 at its upper end and an inwardly tapered portion 30 at its lower end. A reduced diameter, solid extension or post 32 projects downwardly from tapered portion 30 and has outwardly projecting, annular ribs 34 to provide increased surface area for bonding to the tooth material. The socket 25 is of stepped diameter, having a reduced diameter portion 36 adjacent tapered rim 28, an increased diameter, annular groove portion 38 below portion 36, and a tapered lower end portion 39. A V-shaped centering notch 37 is provided at the lower, flat end of the socket.

The stud 20 is of a material having some resilience, preferably nylon plastic, and has a central shaft portion 40 with first and second heads 42,44 at opposite ends of the shaft portion. The first head 42 is shaped and dimensioned to match the shape and dimensions of socket 25, and is designed for releasable snap engagement in the socket. Thus, head 42 has an annular ring or band portion 46 of diameter substantially matching that of ring portion 38 of the socket, and a tapered portion 48 for fitting in tapered portion 39 of the socket. Ring portion 46 has a flat 47, as illustrated in FIG. 1. The shaft portion 40 has a diameter substantially matching that of the smaller diameter portion 36 of socket 25. The second head 44 at the opposite end of the pin 20 has a part-spherical portion 50 and a curved upper end surface 52.

Retainer ring or sleeve 22 has a through bore designed to slide over shaft portion 40. The through bore has an upper portion 54 of part-spherical shape matching that of the part-spherical portion 50 of head 44, forming a seat for head 44, as best illustrated in FIG. 2. Thus, the head 44 and retainer ring 22 together form a swivel or hinge joint with the head 44 swivelling or pivoting relative to swivel seat 54 as illustrated in FIG. 3. The lower portion 56 of the through bore is of outwardly tapered shape. The outer surface of retainer ring 22 is generally cylindrical, with an increased diameter ring portion 58 adjacent the lower end of ring 22. A notch 59 is cut out in the lower end of the ring 22. The retainer ring is also formed of a flexible material such as nylon plastic.

Cap 18 has an internal socket 60 shaped to match the outer surface of retainer ring 22 such that retainer ring 22 is a snap lock fit in the socket. The socket has a curved inner or upper end 62 substantially matching the curvature of the upper end surface 52 of head 44. A gap 63 is provided between surfaces 52 and 62 to allow greater freedom of movement and less wear between the parts. The remainder of the socket is substantially cylindrical with a diameter matching that of ring 22. An increased diameter ring or groove portion 64 is provided adjacent the lower end of the cap for receiving ring portion 58. The outer surface of the cap has an upper rim 66 with a flat 67, a reduced diameter groove 68, and a cylindrical skirt portion 69. The cap is of relatively strong, rigid material, such as gold-plated stainless steel.

Centering sleeve 24 is a disc-shaped member having a central opening 70 for fitting over post or pin 20, and has an outer diameter greater than that of the other parts. Centering sleeve is also of flexible material such as nylon plastic, and is intended for use only on installation of the anchor assembly.

The installation procedure for installing the anchor assembly 10 at a selected location in a patient's oral cavity will now be described. The basic procedure is more or less identical to that used for previous Zest anchors as manufactured by Zest Anchors Inc. of Escondido, Calif., and as described in U.S. Pat. No. 3,787,975 referred to above. Firstly, each non-vital tooth in which an anchor is to be installed is reduced to the gingival level. Next, a hole is drilled with a suitably shaped drill matching that of female or socket part 16, forming a full 360° recessed seat on the occlusal surface of the dental root 14. The metal female part 16 is then cemented in the recessed seat, and any final root contouring is completed as necessary in the dental office.

The male part can be installed either in the laboratory or in the dental office, as is conventional in anchor installations. For installation in the laboratory, an impression male 21, as illustrated in FIG. 4, is snapped into the or each metal female previously secured in the oral cavity, the male seating flush on the end flange 29 of the socket. The impression male is of the same nylon plastic material as the male stud, and has a head of shape and dimensions corresponding to the head 42 although ring portion 49 is of smaller diameter than male stud ring portion 46 so that it can be removed more easily from the female socket. The upper end of the impression male has spaced, relatively large diameter flanges 71, 72 for retention in the impression material. Once the central flange 72 has been seated against flange 29 of the female socket, an impression is then taken, exercising caution not to compress the soft tissue surrounding the impression site. The impression males are designed with minimum compression, so that they will be drawn out of the sockets with the impression.

Once the impression has been taken, substitute model females 73, are placed over the males in the impression, as illustrated in FIG. 4, and a master model is then poured. The female substitutes have sockets 74 of shape corresponding to that of the female part 16. The female substitutes in the master model are then an accurate transfer of the position in the oral cavity. The impression is then removed from the master model or cast.

The male part or pin 20 will be supplied assembled with upper end 44 secured to the cap 18 via retainer ring 22, i.e. as illustrated at the upper end of the pin in FIG. 2. The retainer ring 22 is a snap lock in the cap 18, so that once the two parts have been snapped together, they cannot be separated. The lower end of an assembled male part is installed in each substitute model female, with a centering sleeve 24 located on shaft 40 between female 73 and head 44. The caps 18 are then bonded into suitably prepared recesses in the dental appliance, and the appliance and attached male parts are removed from the model. The ends 42 of each male part in the appliance can then be snapped into the sockets 25 of each female part in the oral cavity, after removing centering sleeve 24.

Alternatively, installation can be completed in the dental office. After cementing each female part into prepared tooth recesses, a male part is snapped into each female part. Each male part is assembled with retainer ring 22 and cap 18, and with a centering sleeve 24 positioned on shaft 40 as illustrated in FIG. 2. A recess is cut or a lingual window is prepared in the denture or other dental appliance for receiving the cap of each assembled male part. A suitable adhesive such as a self-curing acrylic resin is placed in the relieved area of the denture. The adhesive is also painted onto the outer surface of the metal cap 18. The appliance is then inserted into position in the oral cavity, and the acrylic is allowed to set without compression of the soft tissue surrounding each anchor site, as illustrated in FIG. 2. The flat 67 on the rim of cap 18 will resist rotation of the cap when secured in the denture recess.

After the acrylic is set, the appliance is removed by snapping the lower ends of each male part out of the corresponding sockets. The centering sleeves 24 are then removed and discarded. The acrylic is then relieved over the remaining root surface so that there is no contact between the root and acrylic saddle. The dental appliance can then be installed by snapping the ends 42 of the or each male into the appropriate socket, and removed for cleaning purposes by snapping out of the sockets.

The engagement of the opposite ends of the male part or pin into the respective sockets is such that there is some movement permitted at both ends of the anchor assembly, providing a double hinging action. However, the majority of movement is provided at the denture rather than the female socket, reducing wear. The lower end or head 42 of the pin is a releasable snap fit in the socket 25, and is rotatable relative to the socket about the axis of the pin, with little or no tilting permitted. Flat 47 provides an escape path for saliva which might otherwise become trapped in the socket.

The part spherical surface 50 at the upper end or head 44 hinges relative to the corresponding, part-spherical seat 60 of retainer ring 22, while retainer ring 22 is a snap lock fit in the socket 60 of cap 18. The recess or slot 59 in the periphery of the lower end of retainer ring 22 allows the ring to flex and compress while being forced into the socket, and the ring will then spring out so that the enlarged ring portion 58 at the lower end locks into groove 64, as illustrated in FIGS. 2 and 3, and cannot be drawn out of the cap due to annular rim 65 of the socket. Thus, the retainer ring 22 locks the head 44 of pin 20 into the socket, and the pin 20 has a rotatable, pivoting or swivel engagement with ring 22, forming a swivel joint, so that a denture 12 attached to cap 18 can hinge or pivot relative to the pin 20 and thus the attached root 14, as illustrated in FIG. 3. With this arrangement, more movement is provided at the denture end of the pin 20 than at the root end 42, reducing wear of the attachment surfaces at the lower end 42, which must be repeatedly snapped into and out of the female part.

This arrangement allows movement of the denture or dental appliance relative to the anchor point or points in the jaw in a manner similar to a universal joint, reducing stress on the anchor. The denture will tend to move in a horizontal plane, sliding over the jaw and tending to keep in contact with the underlying tissue more than with previous anchors, reducing food trapping between the denture and underlying gum areas. Rotation of the denture will be limited by the part-spherical shape of the hinge surface 50, and will be stopped at the lower end 75 of the spherical surface at the position illustrated in FIG. 3. The tapered portion 56 of the retainer ring through bore permits the swivelling motion of the pin 20 relative to ring 22, as can be seen in FIG. 3. By allowing rotational movement of the denture at the attachment of the denture to the pin 20, rather than at the attachment to the root 14 as with previous anchor assemblies, sideways movement of the denture is permitted without causing side force or stress on the tooth.

A gap or space 76 is provided between the lower end of head 42 and the lower end of socket 25, as illustrated in FIGS. 2 and 3. This gap provides an up and down cushion due to the vertical resiliency of the pin when biting pressure is applied to the denture. Only a very small amount of pivoting or rotation relative to the plane of the denture is permitted at the lower end of the pin 20, so as to limit wear of the device.

The design of the metal female socket part 16 and plastic male parts comprising pin 20 and retainer ring 22 is such that increased wear areas are provided between the female socket and male head 42, and between the cap and retainer ring, allowing for a longer attachment life before replacement is necessary as compared with conventional ball and socket configurations. Thus, annular ring portion 46 of the pin provides a relatively long, enlarged area retention band against the corresponding ring or groove portion 38 of socket 25, reducing wear and resultant loosening of the attachment as compared to a spherical ball and socket type of attachment. Preferably, the length of retention band portion 46 is around 0.020 inches. The tapered end 48 of head 42 provides a lead in bevel that allows easy location and fitting of the head into the socket for repeated removal and reinsertion. The diameter of the male shaft 40 is increased in order to reduce bending and breakage.

The tapered portion 30 of female part 16 is an anatomical taper, and this in combination with the reduced diameter post 32 will allow the part to be fitted into small and curved roots more easily. The coating of titanium nitride on the inner and outer surfaces of the female part further increases wear resistance. The coating is preferably 2 to 3.5 microns in thickness.

Preferably, the anchor assembly is made in two different sizes, standard and mini, for fitting different size roots. In one example of a standard anchor assembly, the cover cap snap lock recess or groove 64 had a diameter of 0.140 inches, while the annular rim or flange 65 below recess 64 had a diameter of 0.121 inches. The diameter of the corresponding snap lock ring portion 58 of retainer ring 22 was 0.128 inches. Thus, ring portion 58 must be compressed to be forced past rim 65 into recess 64, and will then expand out so that it cannot be pulled back out of the recess. In contrast, the opposite end 42 of the pin or stud 20 is designed for releasable snap engagement in female part 16. The ring portion 46 of head 42 in this example had a diameter of 0.083 inches while the corresponding diameter of annular groove portion 38 of the female socket 25 was 0.090 inches, and the diameter of portion 36 was 0.0824 inches, so that ring portion 46 can be pulled back out of the socket 25 as necessary.

The diameter of shaft portion 40 was 0.075 inches, which is around 30% larger than used in previous arrangements. This significantly reduces bending and breakage of the part, and increases the lifetime of the male part. Wear on the male part is also reduced by the design of the retention band, which dramatically improves wear resistance.

The components of the mini anchor assembly will be of corresponding shape and operation to the standard anchor, but with reduced dimensions. The mini female will be shorter than the standard female, and of smaller diameter for fitting into smaller root areas. The mini male will have a correspondingly smaller diameter at its end which snap engages in the female socket. In one specific example, a standard female had an overall length of 0.145 inches, an outer diameter of 0.100 inches in cylindrical portion 26, and a socket ring portion of diameter 0.090. The mini female had an overall length of 0.092 inches, with the stem portion being considerably shorter than stem portion 32 and having only one rib 34, an outer diameter of 0.082 in cylindrical portion 26, and a socket ring portion of diameter 0.068 inches. The mini male stud had a ring portion 46 at its end 42 of correspondingly reduced diameter for fitting into the mini socket, specifically around 0.0636 inches.

If the male part 20 should fail or reach the end of its useful lifetime, it can be removed and replaced readily without removing any of the denture acrylic. The male part is simply cored out of the retainer ring 22 using a suitable coring tool. The resilient retainer ring can then be collapsed, using a blade or other pointed instrument, and removed from the cap socket, leaving the metal cap in place in the denture. A suitable seating tool is then used to firmly snap a replacement male 20 and retainer ring 22 into the cap.

Figure 7:
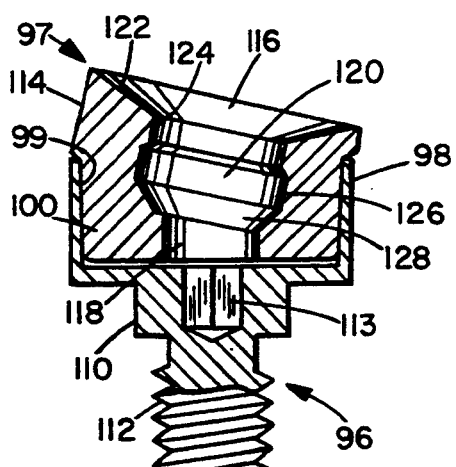
FIG. 7 is a side elevation view, partially cut away, of the assembled components of FIG. 4.
Figure 5:
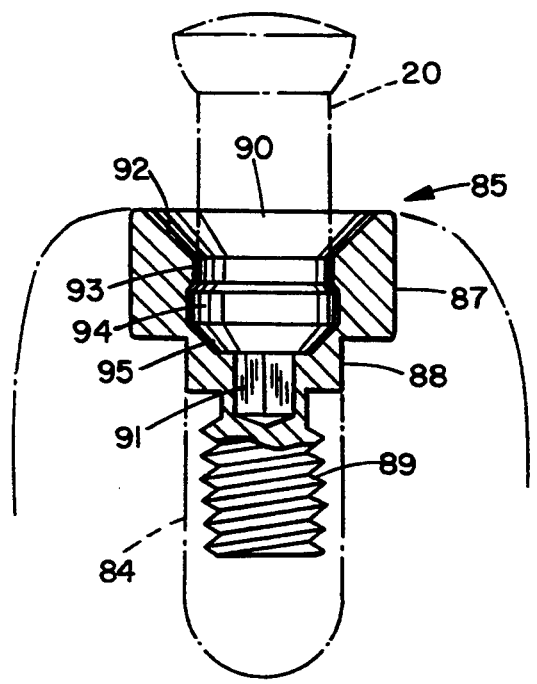
FIG. 5 is a sectioned side view of an alternative female socket element.
Figure 8:
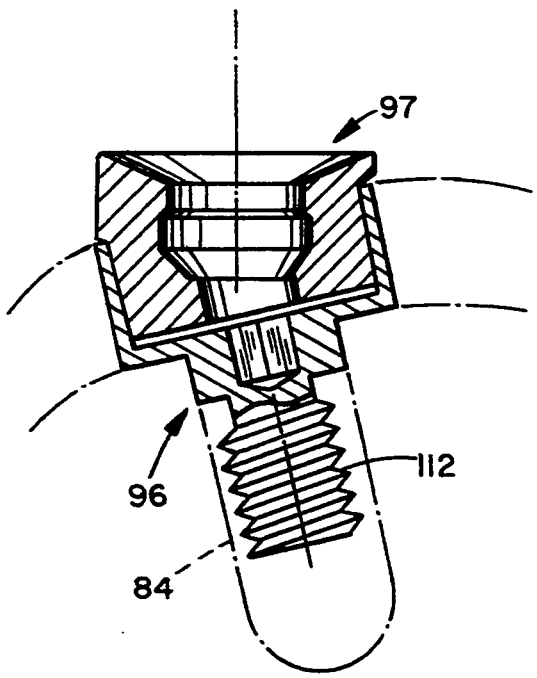
FIG. 8 is a sectional side view of the two part female of FIGS. 6 and 7 assembled with a divergent implant in the jaw.

FIGS. 1–3 illustrate an anchor assembly for attaching a dental appliance 12 directly to an existing non-vital root as an abutment. FIGS. 5–8 illustrate a modification to the female part of the assembly of FIG. 1 for attaching the appliance to an implant 84. The anchor assembly for attaching to an implant is identical to that of FIG. 1 apart from the female part, which is designed to fit a variety of known dental implants. FIG. 5 illustrates a zero angle female 85 for use with straight implants, while FIGS. 6–8 illustrate a two part female 86 for permitting angular adjustment, for use with divergent implants.

The zero angle female 85 is of suitable metal such as titanium alloy coated with a wear resistant coating such as titanium nitride, which is three times harder than the metal alloy itself and extremely bio-compatible. Female part 85 has a cylindrical upper body or cuff 87 having a reduced diameter portion 88, and a downwardly depending threaded stem or abutment 89. Portion 88 and stem 89 are matched to the diameter and thread size of the implant being used, and female parts 85 will be provided for attachment to various known types of dental implants. Thus, portion 88 has a diameter matching the outer diameter of the implant, and threaded stem 89 has a diameter and thread size matching that of the implant bore. Portion 88 may be tapered in alternative embodiments. Thus, zero angle females will be provided with different portions 88 and stems 89 for fitting various standard dental implants.

Female 85 has a socket or recess 90 of identical shape and dimensions to that of the female part 16 of the previous embodiment, but which has a hex bore 91 at its lower end for receiving a suitable internal hex tool for securing female 85 into the implant 84. Socket 90 is designed for releasable snap engagement with the lower end 42 of a male part or stud 20 identical to that used in the previous embodiment, as illustrated in dotted outline in FIG. 4. As in the previous embodiment, socket 90 therefore has a tapered lead-in portion 92, cylindrical portion 93 matching the diameter of shaft portion 40 of the male stud, enlarged diameter ring portion 94 for receiving ring portion 46 of the male stud, and tapered end portion 95.

The anchor assembly for an implant will be otherwise identical to that of the previous embodiment, with a retainer ring 22 for snap lock engagement with cap 18 which can be suitably bonded in a recess in a denture or other dental appliance to hingably secure the opposite end of the male stud 20 to the dental appliance. The female part for attachment to an implant will be provided in at least two different basic diameters, standard and mini, as in the previous embodiment. Additionally, it will be provided in a range of different cuff heights to accommodate different tissue or gum thicknesses, with cuff or cylindrical portion 87 being provided in heights of 3, 4 and 5 mm in one example. When installing the implant female, the tissue thickness is first measured from the apical rim of the implant body to the crest of the gingiva. The female part having the closest possible tissue cuff height to the measured gingival thickness is then selected. When fully threaded into the implant, using an internal hex tool engaging in hex bore 91, the top of the implant female should be level with the surrounding tissue. This provides optimal stress reducing ability due to the subgingival connection of the female to the implant and thus the end of the male part to the implant. If a change in tissue height occurs later, it can be accommodated by unthreading the female part and replacing it with a corresponding part of different cuff height.

FIGS. 6–8 illustrate a two part female 86 for anchoring a dental appliance to a divergent implant 84. The female 86 comprises a base part 96 for securing to the implant and an angled socket part 97 for locking engagement with the base part 96. Base part 96 has a cylindrical body portion 98 similar to body portion 87 of the zero angle part 85, and having a tapered socket 99. Socket part 96 has a correspondingly tapered body portion 100 for locking engagement in socket 99. The socket 99 and portion 100 have a precision machined matching taper known as a Morse taper, so that when the portion 100 is forced into socket 99, it will be permanently locked into the base part 96.

Base part 96 has a lower end portion designed for attachment to a standard dental implant, including reduced diameter portion 110 and threaded stem 112 which are equivalent to portion 88 and stem 89 of the zero angle female of FIG. 4. A hex-shaped bore 113 extends inwardly from the lower end of socket 97, for receiving the end of a suitable tool for insertion of the stem 112 of base part 96 into an implant. It will be understood that base parts 96 will be provided with different lower end portions for fitting different types of standard dental implants.

The angled socket part 97 has an angled upper end portion 114 and a through bore 116 extends through part 97. Through bore 116 has a lower portion 118 which is coaxial with cylindrical cuff 98 and an angled upper socket portion 120. Socket portion 120 is shaped for releasable snap engagement with the lower end 46 of a male stud 20. Thus, as in the previous embodiments, socket portion 120 has a tapered lead in portion 122, cylindrical portion 124 matching the diameter of shaft 40, ring portion 126 of diameter matching that of the snap-in ring portion 46 of stud 20, and lower tapered portion 128. Socket parts 97 will be provided with a range of different angles to allow attachment to divergent implants at varying angles. Preferably, parts 97 are provided with socket portions 120 at angles of 6°, 12°, and 18° to axial bore portion 118. Both parts 96 and 97 are of a suitable metal such as titanium alloy coated with a suitable wear resistant coating such as titanium nitride.

With this arrangement, base part 96 can be secured to a divergent implant 84, so that tapered socket 99 will be at the same angle as the implant, as illustrated in FIG. 8. An appropriate angled socket part 97 is then selected to compensate for this angle, so that socket portion 120 is substantially vertically oriented in the jaw regardless of the angle of the implant. Socket part 97 is first placed loosely in the tapered socket and rotated about its axis until the correct orientation is reached, using a parallel pin having an end for snap engagement in socket 120 to determine when the best alignment is reached both with other abutments and with the path of insertion of the prosthesis. Once the best alignment is achieved, the angled socket part is jammed down into the matching tapered socket, for example by tapping on its end with an appropriate seating tool. The precision machined tapers will permanently lock the two pieces into one. The taper angle is preferably of the order of 1° 30', which is known as a Morse taper. This has been found to create a permanent lock of at least 36 lbs with a tap of as little as 7 lbs. of force. The Morse taper looking engagement between the parts avoids the need to use cement or bonding adhesive between the parts, and makes installation a simple, one-step procedure. This eliminates the need for marking a correct relative position between an insert and socket, then removing the insert to apply cement or adhesive.

The internal hex bore of the base part is still accessible even after an angled insert has been fixed into the base. If a change in tissue height occurs later, it can be accommodated by unthreading the entire unit and replacing it with a base part 96 having different cuff height. Since the hex bore is internal, the unthreading tool does not have to come into contact with any surrounding tissue. This means that the tissue level can be allowed to come up to the top of cuff 98. As in the zero angle female, the base part of the female in the angled version is provided with cylindrical cuff portion 98 of different cuff heights, typically 3 mm, 4 mm and 5 mm, to adjust to individuals having differing tissue thicknesses surrounding the implant site.

The anchor assembly using implant attachment female parts as in FIG. 5 or FIGS. 6–8 is appropriate for use where overdentures or partial dentures are to be retained in whole or part by endosseus implants. The anchor assembly of FIG. 1 is used with appliances where remaining non-vital roots are to be used as direct abutments, and the female part in this embodiment is placed directly into the root, rather than attaching to an implant as in FIG. 5 or 8. In both cases, the subgingival connection of the male stud to the female part results in application of force near the root center of support, and reduced stress as a result.

By providing for movement at both ends of the male part, both at the attachment to the root or implant, and at the attachment to the denture or appliance, a double jointed movement is provided. Both vertical and hinging movement is permitted by the assembly. The slightly flexible male stud cushions occlusal shock and avoids the hard metal-to-metal contact of other attachments, reducing wear. Wear is also reduced by providing the most hinging movement at the top of the male stud rather than where it attaches releasably to the female part. Additional wear reduction is provided by the increased wear areas in the cylindrical retention band of engagement between the plastic male stud and female socket part. This produces a much greater surface area than a cylindrical ball and socket joint where wear typically occurs at a restricted region of the surface. This considerably increases the potential lifetime of the assembly. A further advantage is that worn males can be easily removed and replaced without removing denture acrylic.

Although some preferred embodiments of the invention have been described above by way of example only, it will be understood by those skilled in the field that modifications may be made to the disclosed embodiments without departing from the scope of the present invention, which is defined by the appended claims.

We claim:

1. An anchor assembly for attaching a dental appliance to a tooth root or tooth implant, comprising:
   a female socket member for insertion in a tooth root or implant, the socket member having a first socket;
   a male stud member having an elongate shaft with opposite first and second ends, a head at the first end of the shaft for releasable snap engagement in the first socket to allow relative movement between the stud member and first socket, and a swivel joint at the second end of the shaft;
   securing means for securing the swivel joint in a recess in a dental appliance, the swivel joint comprising means for permitting swivelling of the stud member relative to the dental appliance, the amount of motion permitted by the swivel joint being greater than that permitted between the head and the first socket;
   a cap for securing in a recess in a dental appliance, the cap having a second socket, the second socket and the swivel joint having interchangeable retainer means for retaining the swivel joint in the socket; and
   the interchangeable retainer means comprising snap lock formations for snap lock engagement of the swivel joint in the second socket.

2. The assembly as claimed in claim 1, wherein the swivel joint comprises a pivot head at the second end of the shaft having an at least partially spherical surface, and a separate retainer ring surrounding said pivot head and having an at least partially spherical annular surface for swivel engagement with said at least partially spherical surface of said pivot head.

3. The assembly as claimed in claim 1, wherein the head at the first end of the stud member is rotatable relative to the first socket.

4. An anchor assembly for attaching a dental appliance to a tooth root or tooth implant, comprising:
   a female socket member for insertion in a tooth root or implant, the socket member having a first socket;
   a male stud member having an elongate shaft with opposite first and second ends, a head at the first end of the shaft for releasable snap engagement in the first socket to allow relative movement between the stud member and first socket, and a swivel joint at the second end of the shaft;

securing means for securing the swivel joint in a recess in a dental appliance, the swivel joint comprising means for permitting swivelling of the stud member relative to the dental appliance, the amount of motion permitted by the swivel joint being greater than that permitted between the head and first socket;

a cap for securing in a recess in a dental appliance, the cap having a second socket, the second socket and the swivel joint having interchangeable retainer means for retaining the swivel joint in the socket; and the swivel joint comprises a two part hinge, a first hinge part comprising a head formed integrally at said second end of the pin member and a second hinge part being hingably engaged with said first hinge part and comprising means for snap engagement in said second socket.

5. The assembly as claimed in claim 4, wherein the second hinge part comprises an annular retainer ring encircling said head, the head and retainer ring having opposing, at least partially spherical hinge surfaces, and the ring having an outer surface shaped for snap engagement in said second socket.

6. The assembly as claimed in claim 5, wherein said second socket includes a cylindrical portion, an annular ring portion of diameter larger than that of said cylindrical portion, and an outer rim portion of diameter larger than that of said cylindrical portion, and the outer surface of said ring being shaped and dimensioned to substantially match the shape and dimensions of said second socket.

7. The assembly as claimed in claim 6, wherein said ring has a cut out slot for allowing said ring to be compressed for snap lock engagement in said socket.

8. An anchor assembly for attaching a dental appliance to a tooth root or tooth implant, comprising:

a female socket member for insertion in a tooth root or implant, the socket member having a first socket;

a male stud member having an elongate shaft with opposite first and second ends, a head at the first end of the shaft for releasable snap engagement in the first socket to allow relative movement between the stud member and first socket, and a swivel joint at the second end of the shaft;

the male stud member being of resilient material and the female socket member being of metal; and securing means for securing the swivel joint in a recess in a dental appliance, the swivel joint comprising means for permitting swivelling of the stud member relative to the dental appliance, the amount of motion permitted by the swivel joint being greater than that permitted between the head and first socket.

9. An anchor assembly for attaching a dental appliance to a tooth root or tooth implant, comprising:

a female socket member for insertion in a tooth root or implants the socket member having a first socket;

a male stud member having an elongate shaft with opposite first and second ends, a head at the first end of the shaft for releasable snap engagement in the first socket to allow relative movement between the stud member and first socket, and a swivel joint at the second end of the shaft;

securing means for securing the swivel joint in a recess in a dental appliance, the swivel joint comprising means for permitting swivelling of the stud member relative to the dental appliance, the amount of motion permitted by the swivel joint being greater than that permitted between the head and first socket; and said head having a cylindrical band portion and said first socket having a corresponding first annular portion for receiving said band portion, and a reduced diameter portion for releasably retaining said band portion in said socket.

10. The assembly as claimed in claim 9, including a cap for securing in a recess in a dental appliance, the cap having a second socket, the second socket and the swivel joint having interengageable retainer means for retaining the swivel joint in the socket.

11. The assembly as claimed in claim 9, wherein said band portion has a flat.

12. The assembly as claimed in claim 9, wherein said head has a flat outer end and a tapered portion extending from said band portion to said outer end of said head, and the socket has a flat inner end and a correspondingly tapered portion leading from said annular portion to said flat inner end for receiving the tapered portion of said head.

13. The assembly as claimed in claim 9, wherein said socket member has a cylindrical body and reduced diameter, downwardly depending stem portion extending from said body.

14. The assembly as claimed in claim 13, wherein said stem portion is threaded.

15. The assembly as claimed in claim 13, wherein said stem portion has at least one outwardly projecting annular rib.

16. The assembly as claimed in claim 9, wherein said socket member has a threaded stem portion for attachment to a threaded dental implant.

17. The assembly as claimed in claim 16, including two types of socket members for attachment to a dental implant, the types comprising a zero angle socket member for attachment to a straight implant and an angled socket member for attachment to a divergent implant.

18. The assembly as claimed in claim 17, wherein the zero angle socket member comprises a head portion and a reduced diameter stem portion extending from said head portion, the head portion having a socket aligned with said stem portion for releasable snap engagement with the first end of a pin member.

19. The assembly as claimed in claim 17, wherein the angled socket member is in two parts, comprising a base member having a stem portion for attachment to a dental implant and an inwardly tapered socket having a predetermined taper angle, and an angled abutment member having a tapered outer surface with a taper angle matching that of the tapered socket for permanent locking engagement in said tapered socket, the tapered outer surface having a central axis aligned with said stem portion, and the abutment member having a socket extending at a predetermined angle to said central axis for releasable snap engagement with the first end of a pin member.

20. The assembly as claimed in claim 19, including angled abutment members having sockets at angles of 6°, 12°, and 18° to the central axis of said members.

21. An anchor assembly for attaching a dental appliance to a tooth root or tooth implant, comprising:

a female socket member for insertion in a tooth root or implant, the socket member having a socket;

a male stud member having an elongate shaft with opposite first and second ends, a head at the first end of the shaft for releasable snap engagement in the socket, and the second end comprising means for securing to a dental appliance;

the head having an enlarged cylindrical band portion of larger diameter than the shaft; and the socket having an annular groove portion of dimensions substantially matching those of the cylindrical band portion for releasable snap engagement with said band portion.

22. The assembly as claimed in claim 21 wherein said band portion has a flat region.

23. The assembly as claimed in claim 21, wherein said head has an outer end and an inwardly tapered portion extending from said band portion towards said outer end, the socket having a corresponding inner end and an inwardly tapered portion matching said tapered portion on said head extending from said annular groove portion towards the inner end of said socket.

24. The assembly as claimed in claim 21, wherein said socket has an outwardly tapered rim portion at its outer end, and a reduced diameter portion of diameter substantially matching that of said shaft extending from said tapered rim portion to said annular groove portion.

25. The assembly as claimed in claim 21, wherein said socket has a hex bore at its inner end.

26. The assembly as claimed in claim 21, wherein said socket member has a cylindrical body portion of a first diameter and a reduced diameter stem portion of diameter less than that of said body portion and projecting from said body portion for engagement in a tooth root or implant.

27. The assembly as claimed in claim 21, wherein said band portion on said head comprises a retention band having a height of at least 0.020 inches.

28. The assembly as claimed in claim 21, wherein said shaft has a diameter of at least 0.075 inches.

29. An anchor assembly for attaching a dental appliance to a divergent implant extending at an angle to the desired path of insertion of the appliance, comprising:

a base part having a cuff portion and a stem depending downwardly from the cuff portion, the stem having mating formations for mating engagement with a bore of a divergent implant, the cuff portion having a tapered socket having a predetermined machined taper;

an angled abutment part having opposite first and second ends and a tapered outer surface portion extending from the first end of the part along at least part of the length of the part, the tapered portion having a predetermined machined taper matching that of the tapered socket for permanent locking engagement in said socket when the parts are forced together, the tapered portion having a central axis, and an angled socket extending inwardly from the second end of the abutment part at a predetermined angle to the central axis of said tapered portion; and a stud member for releasably securing the abutment part to a dental appliance, the stud member having a first head at one end for releasable snap engagement in said angled socket, and securing means at the opposite end of the stud for securing the stud member to a dental appliance.

30. The assembly as claimed in claim 29, including a plurality of angled abutment parts having angled sockets extending at different angles to the central axis of the tapered portion.

31. The assembly as claimed in claim 30 wherein the sockets extend at angles of 6°, 12°, and 18° to said central axis.

32. An anchor assembly for attaching a dental appliance to a divergent implant extending at an angle to a desired orientation axis of the implant, the assembly comprising:

a base part for insertion in an implant, the base part having a tapered socket with a first longitudinal axis which will be aligned with the axis of the implant when installed, the socket having a predetermined machined taper;

an abutment part having a first portion for attachment to a dental appliance and a second, tapered portion for insertion in said tapered socket, the tapered portion having a predetermined machined taper matching that of the socket for permanent locking engagement in said socket when said parts are forced together with the axis of said second portion coaxial with the axis of said socket;

the first portion of the abutment part having a longitudinal axis extending at an angle to the axis of said second portion and socket, whereby said abutment part can be freely rotated about the axis of said socket when seated loosely in said socket to vary the orientation of said second portion relative to said socket; and said matching tapers comprising means for permanently locking the parts together when said abutment part is forced into said socket when a desired relative orientation between said second portion and socket is reached.

33. The assembly as claimed in claim 32, wherein said base part has a tool-engaging bore extending downwardly from said socket, the tool-engaging bore having mating formations for mating engagement with an installation tool for installing the base part on an implant or removing the base part from an implant, and the abutment part has a through bore aligned with said tool-engaging bore when said parts are locked together to allow an installation tool to be extended through said bore in said abutment part to engage said tool-engaging bore.

34. The assembly as claimed in claim 33, wherein said tool-engaging bore is a hexagonal bore.

35. The assembly as claimed in claim 32, wherein said tapers are Morse tapers.

36. An anchor assembly for attaching a dental appliance to a divergent implant, comprising:

a base part having securing means for releasably securing the base part to an implant extending at an angle to a desired orientation direction of a dental appliance to be secured to the implant, the base part having a socket;

an angled abutment part having a first portion for engagement in said socket at a selected orientation relative to said base part, and a second portion extending at an angle to said first portion, the second portion having coupling means for coupling said abutment part to a dental appliance;

securing means for securing said abutment part to said base part at a selected relative orientation between said parts;

the socket having an inner end, and a tool-engaging bore projecting from the inner end of said socket, the tool-engaging bore having mating formations for mating engagement with a tool for securing the base part to an implant or releasing the base part from the implant; and the abutment part having a through bore aligned with said tool-engaging bore when the parts are secured together, whereby a tool can be inserted into said tool-engaging bore when said parts are secured together via said through bore.

37. The assembly as claimed in claim 36, wherein said tool-engaging bore is a hexagonal bore.

38. A method of anchoring a dental appliance to a divergent implant, comprising the steps of:

securing a stem portion of a base part into a bore of divergent implant, the base part having a tapered socket;

placing a tapered portion of an angled abutment loosely into the tapered socket of the base part, the tapered portion and tapered socket having matching tapers;

rotating the abutment relative to the socket until an angled socket in the abutment is oriented substantially in alignment with a desired path of insertion of a dental appliance;

with the angled socket at the desired orientation, forcing the tapered portion of abutment into the tapered socket until the abutment is permanently locked into the socket; and releasably securing one end of a male part into the angled socket whereby a dental appliance attached to the other end of the male part is anchored to the implant.

* * * * *